United States Patent

Noguchi et al.

[11] Patent Number: 5,133,209
[45] Date of Patent: Jul. 28, 1992

[54] APPARATUS FOR MEASURING GRINDABILITY OF POWDER MATERIAL

[75] Inventors: Takeki Noguchi, Chita; Mitsunori Watanabe, Tokoname, both of Japan

[73] Assignees: Chubu Electric Power Co., Inc.; NGK Insulators, Ltd., both of Japan

[21] Appl. No.: 665,956

[22] Filed: Mar. 8, 1991

[30] Foreign Application Priority Data

Mar. 12, 1990 [JP] Japan .................... 2-60512

[51] Int. Cl.⁵ .................................... G01N 3/56
[52] U.S. Cl. ................................ 73/78; 73/7; 73/818
[58] Field of Search .............. 73/7, 78, 821, 866, 73/87, 818

[56] References Cited

U.S. PATENT DOCUMENTS

| | | | |
|---|---|---|---|
| 1,944,353 | 1/1934 | Linder | 73/78 |
| 2,367,838 | 1/1945 | Allen | 73/7 |
| 3,053,073 | 9/1962 | Baughman | 73/7 |
| 4,676,094 | 6/1987 | Hoffmann et al. | 73/78 |
| 4,898,037 | 2/1990 | Allen et al. | 73/866 |

Primary Examiner—Hezron E. Williams
Assistant Examiner—Howard Wisnia
Attorney, Agent, or Firm—Parkhurst, Wendel & Rossi

[57] ABSTRACT

An apparatus for measuring grindability of a powder material comprises a chute for feeding particles to be measured one at a time, a pair of opposed rolls arranged under the chute so as to receive the particle from the chute in a gap between the opposed rolls, one of the opposed rolls having a stationary shaft which is rotatably supported at a fixed position and the other roll having a movable roll shaft which is rotatably supported on the upper end of an L-shaped arm which is pivoted at the corner thereof to a frame, a rigid base opposed to the other end of the L-shaped arm, a device for adjusting the level of the rigid base, and a load cell interposed between the other end of the arm and the rigid base.

7 Claims, 3 Drawing Sheets

FIG_1

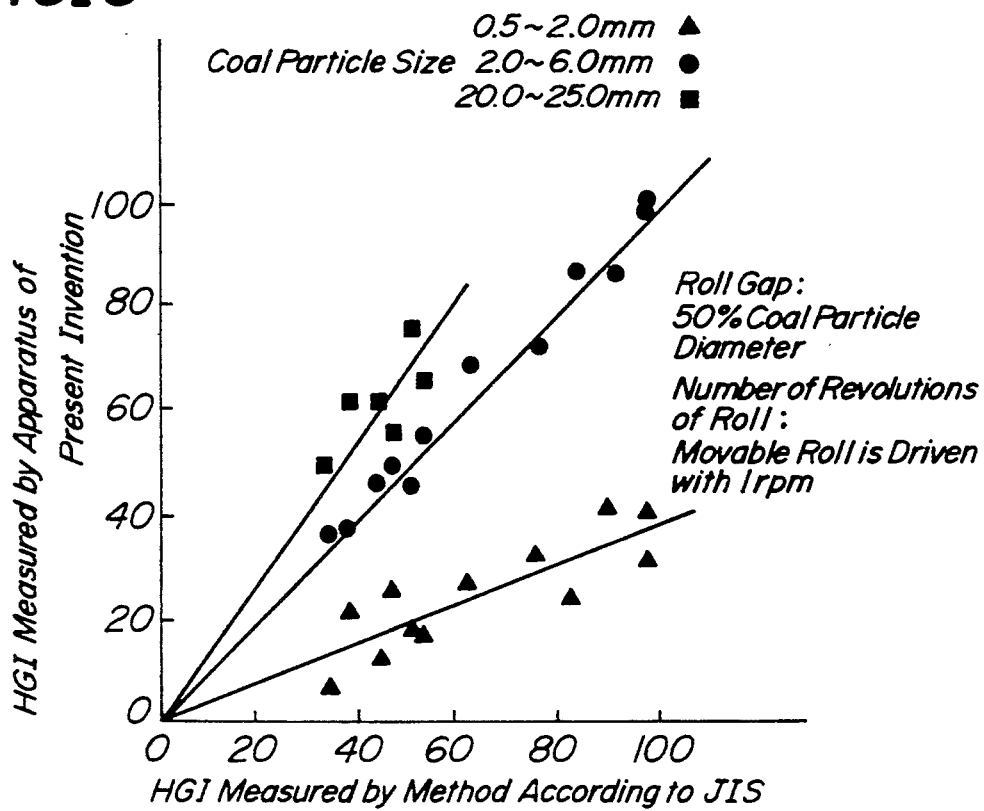
FIG_3
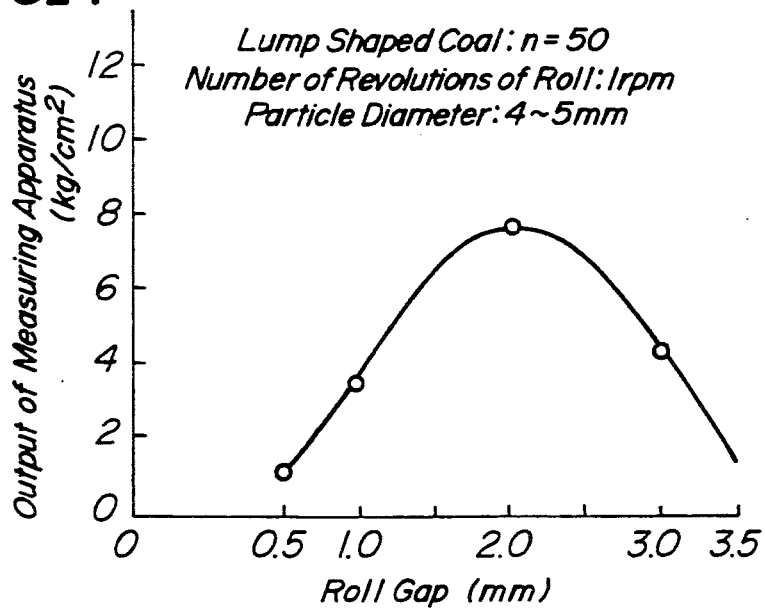
FIG_4

APPARATUS FOR MEASURING GRINDABILITY OF POWDER MATERIAL

BACKGROUND OF THE INVENTION

1. Industrially Applicable Field

The present invention relates to an apparatus for measuring grindability of powder material of coal or the others quickly and accurately.

2. Prior Art

For example, a coal powder is utilized as a fuel in thermal powder plants or the like, and such a coal powder is generally used with a predetermined pulverized particle size. In this case, it is necessary to accurately measure and evaluate a grindability of coal powder.

There has been a method of measuring the grindability of coal powder or the like defined by the Japanese Industrial Standard (JIS) M8801 for determining a value called as "Hardgrove grindability index (HGI)" indicating grindability of a powder material such as coal powder or the like. However, the measuring method defined by the JIS requires 30~40 minutes per one measurement of the HGI, so that it can not be applied for a continuous measurement because of a long timed required for the measurement.

DISCLOSURE OF THE INVENTION

An object of the invention is to remove the disadvantages of the prior art measuring method and to provide an apparatus for measuring a grindability of a powder material which can more quickly and accurately measure the grindability of the powder material such as the coal powder than the method of measuring the HGI defined by the JIS, and moreover can obtain a measured value which correctly coincides to a value measured by the method according to the JIS.

According to the present invention, an apparatus for measuring grindability of a powder material comprises a chute for feeding particles to be measured one at a time, a pair of opposed rolls arranged under the chute so as to receive the particle from the chute in a gap between the opposed rolls, one of said opposed rolls having a stationary shaft which is rotatably supported at a fixed position and the other roll having a roll shaft which is rotatably supported on the upper end of an L-shaped arm which is pivoted at the corner thereof, a rigid base opposed to the other end of the L-shaped arm, and a load cell interposed between the other end of the arm and the rigid base.

According to a preferred embodiment of the invention, the apparatus further comprises means for adjusting the level of the rigid base. Preferably, one of the opposed rolls may be driven by means of a motor, while the other roll may be a follower roll. Alternatively, each of the opposed rolls may be driven by mean of a motor.

An apparatus for measuring grindability of a powder material according to the present invention further comprises a particle detector arranged between an outlet of the feeder and the chute to detect a particle fed from the feeder to the chute, a digital indicator connected to the load cell, a controller connected to the particle detector, and means for converting a peak hold value output from the digital indicator to HGI value based on a given correlation formula.

It is noted that the measuring apparatus according to the present invention can measure the grindability of powder of organic material such as coal, feldspar, porcelain stone or the other mineral, synthetic mullite, alumina or the other ceramics as well as inorganic material such as synthetic resin, foods or the like.

The present invention will be described more in detail by referring to drawings illustrating an embodiment of the apparatus for measuring the grindability of coal powder according to the present invention.

BRIEF DESCRIPTION OF THE DRAWINGS

FIG. 3 is a graph showing a relationship between HGI measured by the method according to the JIS and HGI measured by the apparatus according to the present invention; and FIG. 4 is a graph showing a relationship between roll gaps and outputs of the apparatus of the present invention.

DESCRIPTION OF THE PREFERRED EMBODIMENTS

Figure 1:
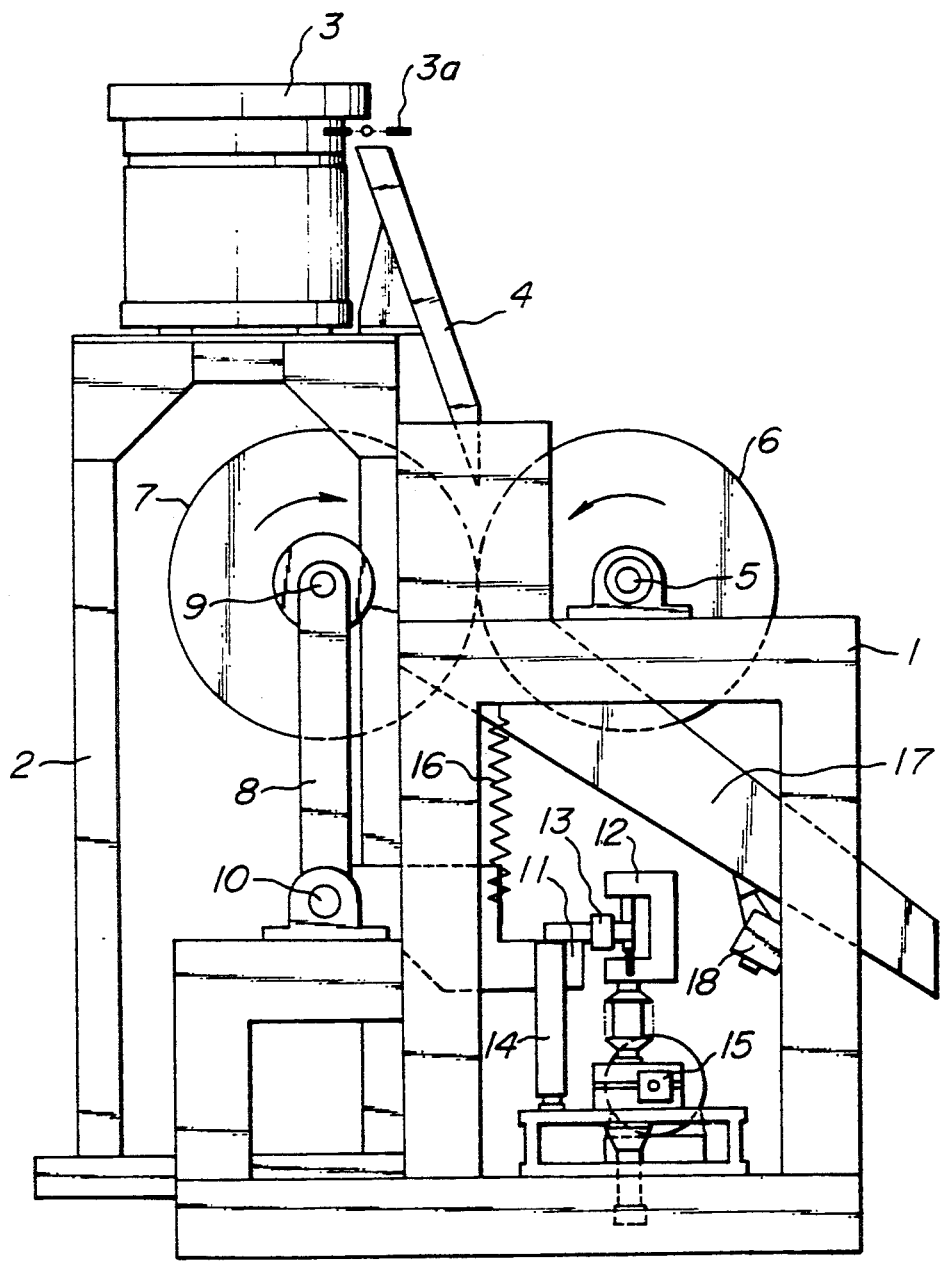
FIG. 1 is a front elevational view illustrating an embodiment of the present invention.

Referring to FIG. 1, an apparatus for measuring the grindability of coal powder includes a frame 1 and a feeder stand 2 provided at a side of the frame. The feeder stand 2 is provided at the upper portion with a feeder 3 for feeding a powder material to be measured and a chute 4.

The feeder 3 is arranged such that a powder material is separated in depending to the size and weight of the particles and each of separated particles is aligned to each other in a spaced condition in the same manner of a parts feeder of a machine tool. The particle preferably has a diameter in a range of 0.5~25 mm, particularly 2~6 mm and is dropped from an end of the feeder 3 to the upper end of the chute 4 one at a time and then fed from the lower end of the chute 4 to a gap between rolls 6 and 7. The chute 4 may be made of a metal such as a stainless steel, wear resistance steel or the like, a ceramics such as silicon carbide, alumina or the like, a metal coated with an organic or inorganic material or a resilient material such as a rubber. Furthermore, the chute 4 is inclined and positioned such that the particle rolls down along the chute and drops from the lower end of the chute to the gap between rolls 6 and 7 without any resistance.

A particle detector 3a such as a photo sensor is arranged between the outlet of the feeder 3 and the upper end of the chute 4 to detect a particle fed to the chute 4 from the feeder 3 and output a detecting signal to a controller 21. The particle detector 3a has an additional function for detecting numbers of particles and outputs an error signal to the controller 21 when more than two particles is erroneously fed to the chute 4 at a time. For this purpose, two particle detectors 3a may be arranged at upper and lower positions. Thus, the particle is effectively fed to the gap between the rolls 6 and 7 one at a time.

The roll 6 has a stationary roll shaft 5 supported by means of bearings fixed to the frame 1 at a position under the chute 4. The roll 7 has a movable roll shaft 9 and is positioned to oppose to the roll 6 in the horizontal direction. In this embodiment, the stationary roll shaft 5 is driven in a direction shown by an arrow by means of a motor (not shown), while the movable roll shaft 9 is rotatably supported on the upper end of an L-shaped arm 8. In this embodiment, the roll 7 is a follower roll without a driving source, but the roller 7 may be driven and the roll 6 is a follower roller or both the rolls may be driven.

In order to be effectively pinched the particle fed from the chute 4 by the rolls 6 and 7, diameters of the roll 6 and 7 are preferably 50~100, preferably 70~10 times of a diameter of the particle to be measured. Furthermore, the gap between the roll 6 and roll 7 is 10~90%, preferably 30~70% of the diameter of the particle and a width of the roll is 5~50, preferably 5~20 times of the diameter of the particle. These rolls may be plane, sand or shot blasted or grooved rolls and made of a wear resistant metal such as S45C steel, a metal having a surface coated with a wear resistant material such as vanadium or a ceramics such as silicon carbide, silicon nitride, alumina or the like.

Furthermore, number of revolutions of the roll is preferably 1~2 rpm and the roll may be rotated only when the particle is fed to the gap between rolls or continuously rotated.

The arm 8 supporting the roll 7 should be made of a material having a sufficient strength to resist against bending thereof and is pivoted at the corner of L-shape to the frame 1 by a shaft 10 so as to be slightly displaced about the shaft 10 by a reaction force generated when the particle fed from the chute 4 pass the gap between the rolls 6 and 7.

In order to detect such a displacement of the arm 8, the other end 11 of the arm 8 is presented to a U-shaped rigid base 12 against a load cell 13 which is connected between the end 11 of the arm 8 and the rigid base 12 to detect a displacement of the arm 8 in the form of an electric signal. The other end 11 of the arm 8 is prevented from rocking laterally by mean of posts 14. The rigid base 12 is supported on an electric jack 15 for adjusting the level of the rigid base. The other end 11 of the arm 8 is continuously contacted with the rigid base 12 by means of a spring 16. The rigid base 12, electric jack 15 and spring 16 serve to adjust the roll gap and correct the mechanical zero point of the load cell 13. The particle passed through the roll gap is discharged by a discharging chute 17 with a vibrator 18. The rolls 6 and 7 may be provided with metallic brushes for removing particle adhered to the surfaces of the rolls.

When the grindability of powder material is measured by the above measuring apparatus according to the present invention, firstly, coal particles having diameter of 0.5~25 mm which is previously sieved and supplied to the feeder 3 in an amount of 50~100 particles at a time. Thus the particles are aligned to each other by the feeder 3 and dropped to the chute one at a time.

Figure 2:
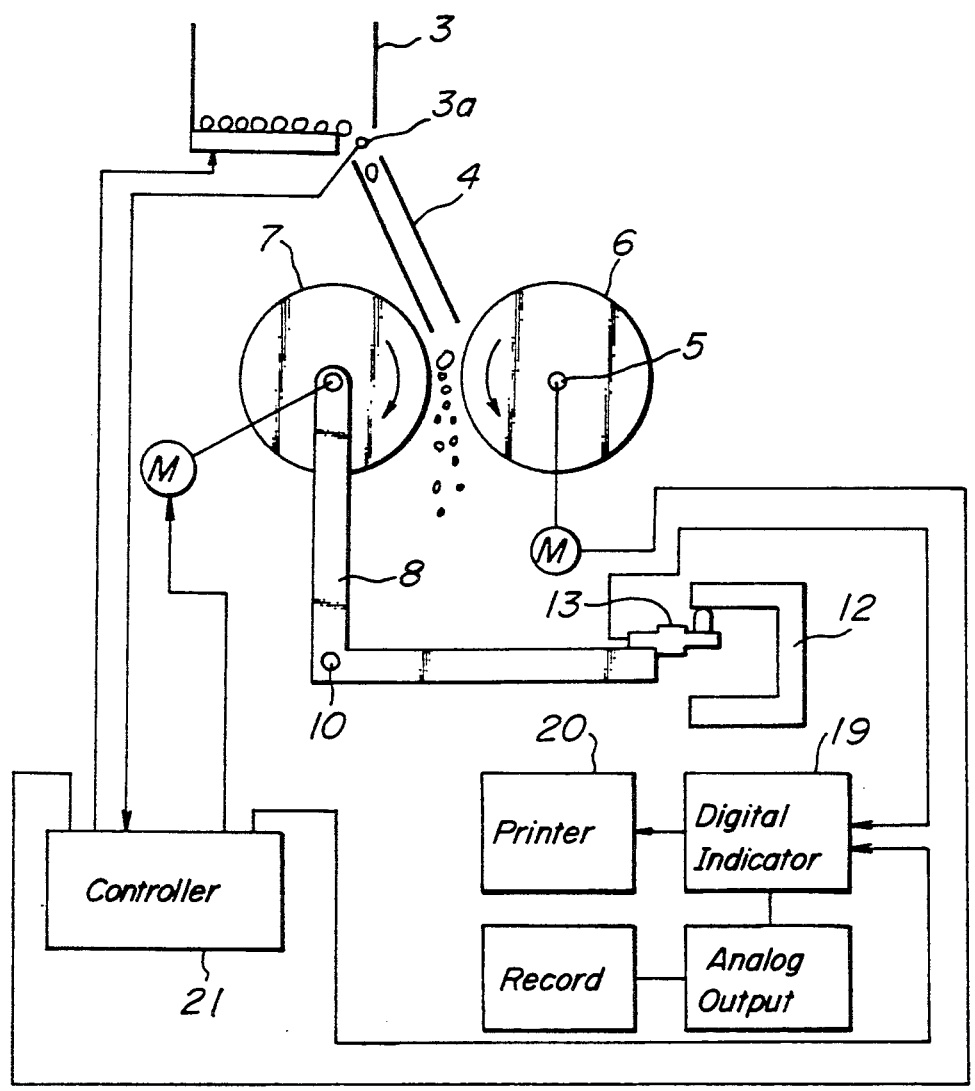
FIG. 2 shows a principle of an operation of the apparatus according to the present invention.

The dropped particle is detected by the particle detector 3a and then the controller 21 shown in FIG. 2 begins measurement of grindability.

The dropped particle is pinched between the roll 6 which is rotated at a constant speed and the roll 7 and passed through the roll gap by pushing away the roll 7 having the movable shaft in responding to the grindability of the particle. At this time, if the particle is difficult to be pulverized, the roll 7 is subjected to a large reaction force and greatly displaced, while if the particle is easy to be pulverized, the roll 7 is subjected to a small reaction force and hardly displaced. Thus, the reaction force subjected by the roll 7 during pulverizing of particle is detected by the load cell 13 interposed between the end 11 of the arm 8 and the rigid base 12. A peak hold value of the reaction force detected by the load cell is input to a digital indicator 19, then converted to HGI based on a given correlating formula by the controller 21 and output by a printer 20 or the like. Thus, the grindability of the particle can be measured in the form of a value of HGI.

It is noted that levels of maximum and minimum values of grindability of powder materials are generally previously known. Accordingly, it is preferable that a peak hold value larger than five times of the maximum value or smaller than one tenth of the minimum value is not counted as an extraneous value. When the particle detector 3a detects more than two particles which are dropped at a time as mentioned before, the measured value is cut. Additionally, means for measuring each particle size may be arranged at a previous stage to correct the measured value depending on the particle size to thereby perform an accurate measurement.

In order to confirm effect of the present invention, a test was carried out for twelve kinds of coal powders. It was confirmed from the result of the test that data obtained by the measuring apparatus of the present invention are satisfactory mated with HGI measured by the method according to the JIS as shown in the graph of FIG. 3. Particularly, when the particle size of coal powder was in a range of 2.0~6.0 mm, the measured data were more satisfactory matched with HGI measured according to the JIS. Moreover, the method according to the JIS required 30~40 minutes per one measurement, while the measuring apparatus of the present invention required only ten minutes per one measurement.

FIG. 4 shows a result of a test carried out for coal particles having diameters of 4~5 mm to examine relationship between the roll gap and output of the measuring apparatus of the present invention. It is seen from FIG. 4 that when the roll gap is set to 50% of the diameter of coal particle, a superior sensibility can be obtained. Therefore, an accurate measurement value can always be obtained by adjusting the roll gap according to the particle size of the powder material.

According to the present invention as described above, the grindability of the powder material such as coal powder can be measured in a very short time and further the measurement value substantially coincided with HGI measured by the method according to the JIS can be quickly obtained. Therefore, the measuring apparatus of the present invention is suitable for continuously measuring the grindability of powder material.

What is claimed is:

1. An apparatus for measuring grindability of a powder material comprising a chute for feeding particles to be measured one at a time, a pair of opposed rolls arranged under the chute so as to receive the particle from the chute in a gap between the opposed rolls, one of said opposed rolls having a stationary shaft which is rotatably supported at a fixed position and the other roll having a movable roll shaft which is rotatably supported on the upper end of an L-shaped arm which is pivoted at the corner thereof, a rigid base opposed to the other end of the L-shaped arm, and a load cell interposed between the other end of the arm and the rigid base for measuring a displacement force; said force indicative of the grindability of said powder material.

2. The apparatus claimed in claim 1, further comprising means for adjusting the level of the rigid base.

3. The apparatus claimed in claim 1, wherein one of the opposed rolls is driven by means of a motor, while the other is a follower roll.

4. The apparatus claimed in claim 1, wherein each of the opposed rolls is driven by means of a motor.

5. The apparatus claimed in claim 1, further comprising supporting posts for preventing the other end of the L-shaped arm from rocking laterally.

6. The apparatus claimed in claim 1, further comprising a particle detector arranged between an outlet of the feeder and the chute to detect a particle fed from the feeder to the chute.

7. The apparatus claimed in claim 6, further comprising a digital indicator connected to the load cell, a controller connected to the particle detector, and means for converting a peak hold value output from the digital indicator to HGI value based on a given correlation formula.

* * * * *